(12) United States Patent
Hogan, II

(10) Patent No.: US 10,034,875 B2
(45) Date of Patent: Jul. 31, 2018

(54) PRODUCT AND METHOD FOR TREATING DIARRHEA

(71) Applicant: Maregade Rx, LLC, Jackson, MS (US)

(72) Inventor: Reed B. Hogan, II, Jackson, MS (US)

(73) Assignee: Maregrade RX, LLC, Jackson, MS (US)

( * ) Notice: Subject to any disclaimer, the term of this patent is extended or adjusted under 35 U.S.C. 154(b) by 0 days.

(21) Appl. No.: 15/257,674

(22) Filed: Sep. 6, 2016

(65) Prior Publication Data

US 2017/0049770 A1 Feb. 23, 2017

Related U.S. Application Data

(63) Continuation of application No. 14/209,937, filed on Mar. 13, 2014, now Pat. No. 9,717,726.

(60) Provisional application No. 61/782,608, filed on Mar. 14, 2013.

(51) Int. Cl.
A61K 31/495 (2006.01)
A61K 31/341 (2006.01)
A61K 31/426 (2006.01)

(52) U.S. Cl.
CPC .......... *A61K 31/495* (2013.01); *A61K 31/341* (2013.01); *A61K 31/426* (2013.01)

(58) Field of Classification Search
None
See application file for complete search history.

(56) References Cited

U.S. PATENT DOCUMENTS

| | | | |
|---|---|---|---|
| 6,264,984 B1 * | 7/2001 | Hussein | A61K 9/0007 424/464 |
| 8,207,188 B2 | 6/2012 | Nicolaou et al. | |
| 8,207,292 B2 | 6/2012 | Nicolaou et al. | |
| 9,717,726 B2 * | 8/2017 | Hogan, II | A61K 31/495 |
| 2007/0254050 A1 * | 11/2007 | Quart | A61K 31/365 424/725 |
| 2009/0042972 A1 | 2/2009 | Rogowski | |
| 2009/0312358 A1 | 12/2009 | Siddiqi | |
| 2010/0144718 A1 | 6/2010 | Nicolaou et al. | |

FOREIGN PATENT DOCUMENTS

| | | |
|---|---|---|
| AU | 2014239878 | 6/2017 |
| CN | 201480022471.0 | 1/2017 |
| CN | 201480022471.0 | 1/2018 |
| EP | 14722445.5 | 9/2017 |
| EP | 17189072.6 | 11/2017 |
| JP | 2016-502404 | 8/2017 |
| KR | 10-2015-7029028 | 1/2018 |
| WO | 1995/01792 | 1/1995 |
| WO | 2006/041367 | 4/2006 |
| WO | 2008/128115 | 10/2008 |
| WO | 2014/152420 | 9/2014 |

OTHER PUBLICATIONS

Barnes et al. (The Annals of Pharmacotherapy Apr. 1993 vol. 27, p. 464-470).*
U.S. Appl. No. 14/209,937, filed Mar. 15, 2017.
U.S. Appl. No. 14/209,937, filed Jun. 9, 2017.
Schiller, L.R., "Secretory Diarrhea", Current Gastroenterology Reports, vol. 1, issue 5, pp. 389-397, (1999).
Schiller, L.R. et al., "Studies of the prevalence and significance of radiolabeled bile acid malabsorption in a group of patients with idiopathic chronic diarrhea", Gastroenterology, vol. 92, pp. 151-160, (1987).
Fordtran, J.S. et al., "Pathophysiology of chronic diarrhoea: insights derived from intestinal perfusion studies in 31 patients", Clinics in Gastroenterology, vol. 15, No. 3, pp. 477-490, (1986).
Lunardi, C. et al., "Double-blind cross-over trial of oral sodium cromoglycate in patients with irritable bowel syndrome due to food intolerance", Clinical & Experimental Allergy, vol. 21, issue 5, pp. 569-572, (1991).
Fine, K.D. et al., "AGA technical review on the evaluation and management of chronic diarrhea", Gastroenterology, vol. 116, issue 6, pp. 1464-1486, (1999).
O'Sullivan, M. et al., "Increased mast cells in the irritable bowel syndrome", Neurogastroenterology and Motility, vol. 12, pp. 449-457, (2000).
Spiller, R.C. et al., "Increased rectal mucosal enteroendocrine cells, T lymphocytes, and increased gut permeability following acute Campylobacter enteritis and in post-dysenteric irritable bowel syndrome", Gut, vol. 47, pp. 804-811, (2000).
Theoharides, T.C. et al., "Critical role of mast cells in inflammatory diseases and the effect of acute stress", Journal of Neuroimmunology, vol. 146, pp. 1-12, (2004).
Barbara, G. et al., "New pathophysiological mechanisms in irritable bowel syndrome", Alimentary Pharmacology & Therapeutics, vol. 20, supplement 2, pp. 1-9, (2004).
Dunlop, S.P. et al., "Abnormal intestinal permeability in subgroups of diarrhea-predominant irritable bowel syndromes", American Journal of Gastroenterology, vol. 101, No. 6, pp. 1288-1294, (2006).
Barbara, G. et al., "Functional gastrointestinal disorders and mast cells: implications for therapy", Neurogastroenterology and Motility, vol. 18, pp. 6-17, (2006).
Halvorson, H.A. et al., "Postinfectious irritable bowel syndrome-a meta-analysis", American Journal of Gastroenterology, vol. 101, pp. 1894-1899, (2006).
Posserud, I. et al., "Small intestinal bacterial overgrowth in patients with irritable bowel syndrome", Gut, vol. 56, pp. 802-808, (2007).
Lewis, J,T. et al., "Crystal-storing histiocytosis due to massive accumulation of charcot-leyden crystals: A unique association producing colonic polyposis in a 78-year-old woman with eosinophilic colitis", American Journal of Surgical Pathology, vol. 321, No. 3, pp. 481-485, (2007).
Jakate, S. et al., "Mastocytic enterocolitis increased mucosal mast cells in chronic intractable diarrhea", Archives of Pathology & Laboratory Medicine, vol. 130, pp. 362-367, (2006).
Kirsch, R.H. et al., "Histopathological alterations in irritable bowel syndrome", Modern Pathology, vol. 19, pp. 1638-1645, (2006).

(Continued)

*Primary Examiner* — Jeffrey S Lundgren
*Assistant Examiner* — William Y Lee
(74) *Attorney, Agent, or Firm* — Evan Law Group LLC

(57) ABSTRACT

A method of treating diarrhea in a patient includes administering an H1 receptor antagonist and an H2 receptor antagonist to the patient.

17 Claims, 1 Drawing Sheet

(56) References Cited

OTHER PUBLICATIONS

Ramos, L. et al., "Stress-mast cell axis and regulation of gut mucosal inflammation: from intestinal health to an irritable bowel", Med Clin (Barc), vol. 129, No. 2, pp. 61-69, (2007) English Abstract.
Piche, T. et al., "Mast cells and cellularity of the colonic mucosa correlated with fatigue and depression in irritable bowel syndrome", Gut, vol. 57, pp. 468-473, (2008).
Visser, J. et al., "Tight junctions, intestinal permeability, and autoimmunity celiac disease and type 1 diabetes paradigms", Annals—New York Academy of Sciences, vol. 1165, pp. 195-205, (2009).
Walker, M.M. et al., "Duodenal mastocytosis, eosinophilia and intraepithelial lymphocytosis as possible disease markers in the irritable bowel syndrome and functional dyspepsia", Alimentary Pharmacology & Therapeutics, vol. 29, pp. 765-773, (2009).
Thabane, M. et al., "Post-infectious irritable bowel syndrome", World Journal of Gastroenterology, vol. 15, No. 29, pp. 3591-3596, (2009).
Walker, M.M. et al., "Implications of eosinophilia in the normal duodenal biopsy—an association with allergy and functional dyspepsia", Alimentary Pharmacology & Therapeutics, vol. 31, pp. 1229-1236, (2010).
Klooker, T.K. et al., "The mast cell stabiliser ketotifen decreases visceral hypersensitivity and improves intestinal symptoms in patients with irritable bowel syndrome", Gut, vol. 59, pp. 1213-1221, (2010).
Martinez, C. et al., "The jejunum of diarrhea-predominant irritable bowel syndrome shows molecular alterations in the tight junction signaling pathway that are associated with mucosal pathobiology and clinical manifestations", American Journal of Gastroenterology, vol. 107, pp. 736-746, (2012).
Smith, M.J. "IBS remains a mysterious disorder, with few effective remedies", Gastroenterology and Endoscopy News, vol. 63, No. 4, pp. 1-6, (2012).
Pyleris, E. et al., "The prevalence of overgrowth by aerobic bacteria in the small intestine by small bowel culture: relationship with irritable bowel syndrome", Digestive Diseases and Sciences, vol. 57, pp. 1321-1329, (2012).
Vivinus-Nebot, M. et al., "Combination of allergic factors can worsen diarrheic irritable bowel syndrome: role of barrier defects and mast cells", American Journal of Gastroenterology, vol. 107, pp. 75-81, (2012).
Akhavein, A. et al., "Allergic mastocytic gastroenteritis and colitis: an unexplained etiology in chronic abdominal pain and gastrointestinal dysmotility", Gastroenterology Research and Practice, pp. 1-6, (2012).
Martinez, C. et al., "Diarrhoea-predominant irritable bowel syndrome: an organic disorder with structural abnormalities in the jejunal epithelial barrier", Gut, vol. 62, issue 8, pp. 1160-1168, (2013).
Braak, B. et al., "Mucosal immune cell numbers and visceral sensitivity in patients with irritable bowel syndrome: is there any relationship?", American Journal of Gastroenterology, vol. 107, pp. 715-726, (2012).
Theoharides, T.C. et al., "Irritable bowel syndrome and the elusive mast cells", American Journal of Gastroenterology, vol. 107, No. 5, pp. 727-729, (2012).
Farhadi, A. et al., "Mucosal mast cells are pivotal elements in inflammatory bowel disease that connect the dots: stress, intestinal hyperpermeability and inflammation", World Journal of Gastroenterology, vol. 13, No. 22, pp. 3027-3030, (2007).
Juckett, G. et al., "Evaluation of chronic diarrhea", American Family Physician, vol. 84, No. 10, pp. 1119-1126, (2011).
"Diarrhea", National Digestive Diseases Information Clearinghouse, pp. 1-8, (2011).
Forbes, D.A. et al., "Laxative abuse and secretory diarrhoea", Archives of Disease in Childhood, vol. 60, No. 1, pp. 58-60, (1985).
DuPont, H.L. et al., "Diarrhea", National Digestive Diseases Information Clearinghouse, 8 pages, Jan. 2012.
Lever, D.S. et al., "Acute Diarrhea", Cleveland Clinic, Center for Continuing Education publications: Disease Management Project, pp. 1-8, (2010).
MedlinePlus, "H2 blockers", U.S. National Library of Medicine, National Institutes of Health, 3 pages, found at www.nlm.nih.gov/medlineplus/ency/patientinstructions/000382.htm, printed on Feb. 11, 2013.
Runge, J.W. et al., "Histamine antagonists in the treatment of acute allergic reactions" Annals of Emergency Medicine, vol. 21, No. 3, pp. 237-242, (1992).
Lin, R.Y. et al., "Improved outcomes in patients with acute allergic syndromes who are treated with combined $H_1$ and $H_2$ antagonists", Annals of Emergency Medicine, vol. 36, No. 5, pp. 462-468, (2000).
He, S. et al., "Formulation and evaluation of novel coated floating tablets of bergenin and cetirizine dihydrochloride for gastric delivery", Drug Development and Industrial Pharmacy, vol. 38, No. 10, pp. 1280-1288, (2012).
Akin, C. et al., "Mast cell activation syndrome: Proposed diagnostic criteria", Journal of Allergy and Clinical Immunology, vol. 126, No. 6, pp. 1099-1104, (2010).
Hamilton, M.J. et al., "Mast cell activation syndrome: A newly recognized disorder with systemic clinical manifestations", Journal of Allergy and Clinical Immunology, vol. 128, No. 1, pp. 147-152, (2011).
Valent, P., "Mast cell activation syndromes: definition and classification", Allergy, vol. 68, pp. 417-424, (2013).
Simons, F.E. et al., "Second-generation H1-receptor antagonists", Annals of Allergy, vol. 66, No. 1, pp. 5-16, (1991).
Melcescu, E. et al., "The various faces of autoimmune endocrinopathies: Non-tumoral hypergastrinemia in a patient with lymphocytic colitis and chronic autoimmune gastritis", Experimental and Molecular Pathology, vol. 93, Issue 3, pp. 434-440, (2012).
Elvevi, A., et al., "Severe chronic diarrhea and maculopapular rash: A case report", World Journal of Gastroenterology, vol. 17, issue 34, pp. 3948-3952, (2011).
Valent, P. et al., "Standards and standardization in mastocytosis: consensus statements on diagnostics, treatment recommendations and response criteria", European Journal of Clinical Investigation, vol. 37, No. 6, pp. 435-453, (2007).
"Mast cell" found at http://en.wikipedia.org/wiki/Mast_cell, 5 pages, (2014).
Boyce, P.M. et al., "Irritable bowel syndrome according to varying diagnostic criteria: are the new Rome II criteria unnecessarily restrictive for research and practice?", American Journal of Gastroenterology, vol. 95, issue 11, pp. 3176-3183, (2000).
Chey, W.D. et al., "Utility of the Rome I and Rome II criteria for irritable bowel syndrome in US women", American Journal of Gastroenterology, vol. 97, No. 11, pp. 2803-2811, (2002).
Barbara, G. et al., "Mast cell-dependent excitation of visceral-nociceptive sensory neurons in irritable bowel syndrome", Gastroenterology, vol. 132, issue 1, pp. 26-37, (2007).
Kushnir-Sukhov, N.M. et al., "Mastocytosis", Allergy and Allergic Diseases, Second Edition, pp. 1878-1893, (2009).
"How are mast cell issues treated?", Microscopic Colitis Support, 5 pages, found at www.microscopiccolitis.org/articles/How%20are%20mast%20cell%20issues%20treated.html, Apr. 6, 2013.
Stacpoole, P.W. et al., "Combination H1 and H2 receptor antagonist therapy in diabetic autonomic neuropathy", Southern Medical Journal, vol. 75, No. 5, pp. 634-635, (1982).
International Search Report dated Jun. 24, 2014, for PCT application No. PCT/US2014/027323, 9 pages.
Thonhofer, R. et al., "Mastocytic enterocolitis as a rare cause of chronic diarrhea in a patient with rheumatoid arthritis", Wiener klinische Wochenschrift, vol. 123, pp. 297-298, (2011).
Linde, R. et al., "Combination H1 and H2 receptor antagonist therapy in mastocytosis", Annals of Internal Medicine, vol. 92, No. 5, p. 716, (1980).
Lonnroth, I. et al., "Chlorpromazine reverses diarrhea in piglets caused by enterotoxigenic Escherichia coli", Infection and Immunity, vol. 24, No. 3, pp. 900-905, (1979).

(56) References Cited

OTHER PUBLICATIONS

Spiegel, D.R. et al., abstract of "Treatment of irritable bowel syndrome with comorbid anxiety symptoms with mirtazapine", Database Biosis, Biosciences Information Service, vol. 34, 2 pages, (2011).
Berry, E.M. et al., "Carcinoid myopathy and treatment with cyproheptadine (Periactin)", Gut, vol. 15, pp. 34-38, (1974).
Aly, A. et al., "Effect of an H2-receptor blocking agent on diarrhoeas after extensive small bowel resection in crohn's disease", Acta Medica Scandinavica, vol. 207, No. 1-2, pp. 119-122, (1980).
Fondacaro, J.D. et al., "Cecectomized rat—A model of experimental secretory diarrhea in conscious animals", Journal of Pharmacological Methods, vol. 24, pp. 59-71, (1990).
Rabbani, G.H., Abstract of "Mechanism and treatment of diarrhoea due to vibrio cholerae and *Escherichia coli*: roles of drugs and prostaglandins", Database Medline, 2 pages, (1996).
Qin, Z. et al., "Synergistic action of famotidine and chlorpheniramine on acetic acid-induced chronic gastric ulcer in rats", World Journal of Gastroenterology, vol. 11, No. 45, pp. 7203-7207, (2005).
Lorenz, W. et al., abstract of "Studies on the effectiveness of H1-+H2-antagonist combinations in preventing life-threatening anaphylactoid reactions in anaesthesia and surgery: Problems with selecting the animal model from clinical data and with "equi-effective" doses", Database Embase, 2 pages, (1992).
Sultana, N. et al., "In vitro studies of the interaction between cetirizine and H2 receptor antagonists using spectrophotometry and reversed-phase high-performance liquid chromatography", Medicinal Chemistry Research, vol. 19, pp. 462-474, (2010).
International Search Report dated Oct. 9, 2014, for PCT application No. PCT/US2014/027323, 22 pages.
"H2 blockers (acid reducers) for gastroesophageal reflux disease (GERD)", found at www.webmd.com/heartburn-gerd/h2-blockers-acid-reducers-for-gastroesophageal-reflux-disease-gerd, 2 pages, printed on Feb. 11, 2013.
Quigley, E. et al., "Irritable bowel syndrome: a global perspective", World Gastroenterology Organisation Global Guideline, pp. 1-20, (2009).
American Gastroenterological Association, "American Gastroenterological Association medical position statement: Guidelines for the evaluation and management of chronic diarrhea", Gastroenterology, vol. 116, pp. 1461-1463, (1999).
del Cuvillo, A. et al., "Comparative pharmacology of the $H_1$ antihistamines", Journal of Investigational Allergology and Clinical Immunology, vol. 16, supplement 1, pp. 3-12, (2006).
Baker, E.H. et al., "Complications of laxative abuse", Annual Review of Medicine, vol. 47, pp. 127-134, (1996).
Arevalo, F. et al., "Increase of intraepithelial lymphocytes in patients with irritable bowel syndrome", Rev. Gastroenterology Peru, vol. 31, No. 4, pp. 315-318, (2011), English Abstract.
Bleehan, S.S. et al., "Cimetidine and chlorpheniramine in the treatment of chronic idiopathic urticaria: a multi-centre randomized double-blind study", British Journal of Dermatology, vol. 117, issue 1, pp. 81-88, (1987).
Deml, K-F., et al., "Interactions of histamine $H_1$-receptor agonists and antagonists with the human histamine $H_4$-receptor", Molecular Pharmacology, vol. 76, No. 5, pp. 1019-1030, (2009).
DeSilva, A.P. et al., "Subclinical mucosal inflammation in diarrhea-predominant irritable bowel syndrome (IBS) in a tropical setting", Scandinavian Journal of Gastroenterology, vol. 47, No. 6, pp. 619-624, (2012).
Dorsch, W., et al., "Histamine$_1$-histamine$_2$ antagonism: effect of combined clemastine and cimetidine pretreatment on allergen and histamine-induced reactions of the guinea pig lung in vivo and In vitro", Agents and Actions, vol. 12, issue 1-2, pp. 113-118, (1982).
Echizen, H., et al., "Clinical pharmacokinetics of famotidine", Clinical Pharmacokinetics, vol. 21, issue 3, pp. 178-194, (1991).
Flockhart, D.A. et al., "Selection of drugs to treat gastro-oesophageal reflux disease: the role of drug interactions", Clinical Pharmacokinetics, vol. 39, issue 4, pp. 295-309, (2000).

Fogel, W.A. et al., "Histamine in idiopathic inflammatory bowel diseases—not a standby player", Folia Medica Cracoviensia, vol. 46, No. 3-4, pp. 107-118, (2005).
Ford, A.C. et al., "Mucosal inflammation as a potential etiological factor in irritable bowel syndrome: a systematic review", Journal of Gastroenterology, vol. 46, No. 4, pp. 421-431, (2011).
Harvey, R.P. et al., "The effect of $H_1$ and $H_2$ blockade on cutaneous histamine response in man", The Journal of Allergy and Clinical Immunology, vol. 65, issue 2, pp. 136-139, (1980).
Hofstra, C.L. et al., "Histamine $H_4$ receptor mediates chemotaxis and calcium mobilization of mast cells", The Journal of Pharmacology and Experimental Therapeutics, vol. 305, No. 3, pp. 1212-1221, (2003).
Humphries, T.J. et al., "Review article: drug interactions with agents used to treat acid-related diseases", Alimentary Pharmacology & Therapeutics, vol. 13, supplement 3, pp. 18-26, (1999).
Irwin, R.B. et al., "Mediator release in local heat urticaria: protection with combined H1 and H2 antagonists", The Journal of Allergy and Clinical Immunology, vol. 76, issue 1, pp. 35-39, (1985).
Kristjansson, G. et al., "Clinical and subclinical intestinal inflammation assessed by the mucosal patch technique: studies of mucosal neutrophil and eosinophil activation in inflammatory bowel diseases and irritable bowel syndrome", Gut, vol. 53, pp. 1806-1812, (2004).
Lim, H.D. et al., "Evaluation of histamine $H_1$-, $H_2$-, and $H_3$-receptor ligands at the human histamine $H_4$ receptor: identification of 4-methylhistamine as the first potent and selective $H_4$ receptor agonist", The Journal of Pharmacology and Experimental Therapeutics, vol. 314, No. 3, pp. 1310-1321, (2005).
Ling, P. et al., "Histamine $H_4$ receptor mediates eosinophil chemotaxis with cell shape change and adhesion molecule upregulation", British Journal of Pharmacology, vol. 142, pp. 161-171, (2004).
Lippert, U. et al., "Human skin mast cells express H2 and H4, but not H3 receptors", The Journal of Investigative Dermatology, vol. 123, pp. 116-123, (2004).
Matsushita, A. et al., "Advantages of histamine H4 receptor antagonist usage with H1 receptor antagonist for the treatment of murine allergic contact dermatitis", Experimental Dermatology, vol. 21, pp. 710-720, (2012).
Moscati, R.M. et al., "Comparison of cimetidine and diphenhydramine in the treatment of acute urticaria", Annals of Emergency Medicine, vol. 19, issue 1, pp. 12-15, (1990).
Murch, S., "Allergy and intestinal dysmotility—evidence of genuine causal linkage?", Current Opinion in Gastroenterology, vol. 22, issue 6, pp. 664-668, (2006).
Ohsawa, Y. et al., "The antagonism of histamine H1 and H4 receptors ameliorates chronic allergic dermatitis via anti-pruritic and anti-inflammatory effects in NC/Nga mice", Allergy, vol. 67, No. 8, pp. 1014-1022, (2012).
Oksaharju, A. et al., "Probiotic lactobacillus rhamnosus downregulates FCER1 and HRH4 expression in human mast cells", World Journal of Gastroenterology, vol. 17, No. 6, pp. 750-759, (2011).
Paul, E. et al., "Effect of terfenadine and ranitidine on histamine and suxamethonium wheals", European Journal of Clinical Pharmacology, vol. 34, issue 6, pp. 591-594, (1988).
Poli, E. et al., "Functional characterisation of the novel histamine $H_3$ receptor agonist, VUF 5810, on the guinea-pig isolated ileum", Inflammation Research, vol. 53, supplemental 1, pp. S77-S78, (2004).
Reher, T.M. et al., "Incomplete activation of human eosinophils via the histamine $H_4$-receptor: evidence for ligand-specific receptor conformations", Biochemical Pharmacology, vol. 84, issue 2, pp. 192-203, (2012).
Rosenwasser, L.J. et al., "Mast cell stabilization and anti-histamine effects of olopatadine ophthalmic solution: a review of pre-clinical and clinical research", Current Medical Research & Opinion, vol. 21, No. 9, pp. 1377-1387, (2005).
Sander, L.E. et al., "Selective expression of histamine receptors H1R, H2R, and H4R, but not H3R, in the human intestinal tract", Gut, vol. 55, pp. 498-504, (2006).
Simons, F. et al., "Effect of the $H_2$-antagonist cimetidine on the pharmacokinetics and pharmacodynamics of the $H_1$-antagonists

(56) References Cited

OTHER PUBLICATIONS hydroxyzine and cetirizine in patients with chronic urticaria", Journal of Allergy and Clinical Immunology, vol. 95, issue 3, pp. 685-693, (1995).
Stokes, J.R. et al., "The effects of an $H_3$ receptor antagonist (PF-03654746) with fexofenadine on reducing allergic rhinitis symptoms", Journal of Allergy and Clinical Immunology, vol. 129, No. 2, pp. 409-412e2, (2012).
Takeshita, K. et al., "Critical role of L-selectin and histamine H4 receptor in zymosan-induced neutrophil recruitment from the bone marrow: comparison with carrageenan", The Journal of Pharmacology and Experimental Therapeutics, vol. 310, No. 1, pp. 272-280, (2004).
Varga, C. et al., "Inhibitory effects of histamine $H_4$ receptor antagonists on experimental colitis in the rat", European Journal of Pharmacology, vol. 522, issues 1-3, pp. 130-138, (2005).
Walker, M.M. et al., "The role of eosinophils and mast cells in intestinal functional disease", Current Gastroenterology Reports, vol. 13, issue 4, pp. 323-330, (2011).
Wood, J.D., "Histamine, mast cells, and the enteric nervous system in the irritable bowel syndrome, enteritis, and food allergies", Gut, vol. 55, No. 4, pp. 445-447, (2006).
Breunig, E. et al., "Histamine excites neurones in the human submucous plexus through activation of H1, H2, H3 and H4 receptors", The Journal of Physiology, vol. 583, pt. 2, pp. 731-742, (2007).
Rijnierse, A. et al., "Mast cells and nerves tickle in the tummy: Implications for inflammatory bowel disease and irritable bowel syndrome", Pharmacology & Therapeutics, vol. 116, issue 2, pp. 207-235, (2007).
Fasano, A., "Zonulin and its regulation of intestinal barrier function: The biological door to inflammation, autoimmunity, and cancer", Physiological Reviews, vol. 91, pp. 151-175, (2011).
Fedorowicz, Z. et al., "Histamine H2-receptor antagonists for urticaria (review)", Cochrane Database of Systematic Reviews, Issue 3, pp. 1-35, (2012).
De Ponti, F., "Drug development for the irritable bowel syndrome: current challenges and future perspectives", Frontiers in Pharmacology, vol. 4, article 7, pp. 1-12, (2013).
Wald, A. et al., "Pathophysiology of irritable bowel syndrome", UpToDate, 13 pages, Mar. 2016.
Friedling, T. et al., "Diabetic autonomic neuropathy of the gastrointestinal tract", UpToDate, 13 pages, Mar. 2016.
Krishnamurthi, S.S., "Enterotoxicity of chemotherapeutic agents", UpToDate, 15 pages, Mar. 2016.
Riddle, M.S. et al., "ACG Clinical guideline: diagnosis, treatment, and prevention of acute diarrheal infections in adults", The American Journal of Gastroenterology, pp. 1-21, published online Apr. 12, 2016.
Guarino, B., "Abuse of diarrhea medicine you know well is alarming physicians", The Washington Post, Morning Mix, 3 pages, found at www.washingtonpost.com/news/morning-mix/wp/2016/05/04/physicians-alarmed-by-abuse-of-over-the-counter-diarrhea-medicine-you-know-well/, May 4, 2016.

Kushnir-Sukhov, N.M. et al., "Mastocytosis", Allergy and Allergic Disease, 2nd edition, chapter 91, pp. 1878-1893, (2008).
Ishikawa, M. et al., "Drug interaction effects on antitumor drugs. XIII. Amelioration of cisplatin lethality and renal toxicity by chlorpromazine in mice", Biological & Pharmaceutical Bulletin, vol. 16, No. 11, pp. 1104-1107, (1993).
Coupet, J. et al., "Brain histamine H1- and H2-receptors and histamine-sensitive adenylate cyclase: effects of antipsychotics and antidepressants", European Journal of Pharmacology, vol. 74, pp. 149-155, (1981).
European Search Report dated Oct. 31, 2016, for EP application No. 14 722 445.5-1466, 5 pages.
Roch-Arveiller, M. et al., "In vitro effect of cetirizine on PGE2 release by rat peritoneal macrophages and human monocytes", Agents and Actions, vol. 43, pp. 13-16, (1994).
Ahrens, R. et al., "Histamine-induced chloride secretion is mediated via $H_2$-receptors in the pig proximal colon", Inflammation Research, vol. 52, issue 2, pp. 79-85, (2003).
Zhang, L. et al., "Mast cells and irritable bowel syndrome: From the bench to the bedside", Journal of Neurogastroenterology and Motility, vol. 22, No. 2, pp. 181-192, (2016).
Liu, H. et al., "Effects of first and second generation antihistamines on muscarinic induced mucus gland cell ion transport" BMC Pharmacology, vol. 5, No. 8, pp. 1-10, (2005).
Deiteren, A. et al., "Histamine H4 and H1 receptors contribute to postinflammatory visceral hypersensitivity", Gut, vol. 63, No. 12, pp. 1873-1882, (2014).
"Guidance for Industry: Estimating the Maximum Safe Starting Dose in Initial Clinical Trials for Therapeutics in Adult Healthy Volunteers", U.S. Department of Health and Human Services, Food and Drug Administration, Center for Drug Evaluation and Research (CDER), Pharmacology and Toxicology, 30 pages, (2005).
"$H_2$ antagonist" found at http://en.wikipedia.org/wiki/H2_antagonist, 4 pages, 2017.
Ghadir, M.R. et al., "Doxepin is more effective than nortriptyline and placebo for the treatment of diarrhea-predominant irritable bowel syndrome: A randomized triple-blind placebo-controlled trial", Tehran University Medical Journal, pp. 352-358, (2011). (with English Abstract).
"Nortriptyline" found at http://en.wikipedia.org/wiki/Nortriptyline, 10 pages, (2017.
"Search results for doxepin hydrochloride", Drugs & Biologics, 1 page, 2017.
U.S. Appl. No. 15/853,586, filed Dec. 22, 2017.
Doc. No. R 33, pp. 15, dated Mar. 12, 2018, Application No. PCT/US2017/068355, WO.
Doc. No. R36, pp. May 1, 2018, U.S. Appl. No. 15/853,586, US.
Doc. No. R34, pp. 7, dated Mar. 16, 2018, Application No. 2017251701, AU.
International Search Report and Written Opinion dated Mar. 12, 2018, for PCT application No. PCT/US2017/068355, 14 pages.
U.S. Appl. No. 14/209,937, dated Mar. 13, 2014.†

\* cited by examiner
† cited by third party

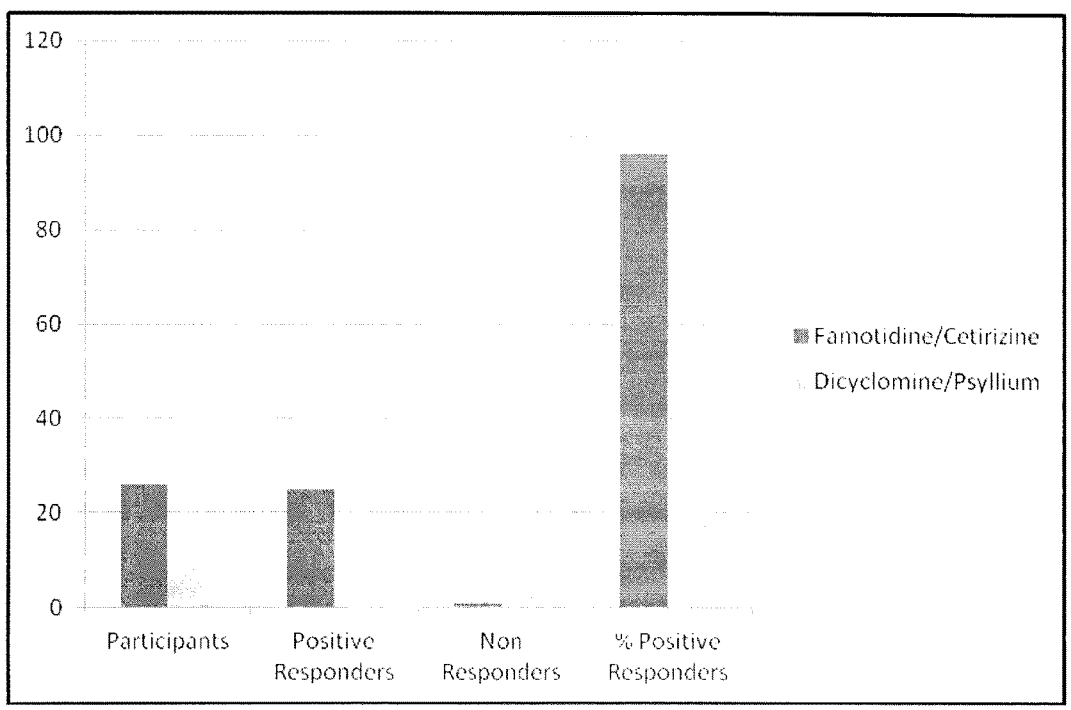

PRODUCT AND METHOD FOR TREATING DIARRHEA

CROSS-REFERENCE TO RELATED APPLICATION

The present application claims the benefit of U.S. Provisional Application No. 61/782,608 filed 14 Mar. 2013, entitled "PRODUCT AND METHOD FOR TREATING DIARRHEA" the entire contents of which are hereby incorporated by reference, except where inconsistent with the present application.

BACKGROUND

Diarrhea is a common condition characterized by increased frequency or fluidity of bowel movements. Diarrhea may cause dehydration and electrolyte abnormalities that may require hospitalization to replace lost fluids and electrolytes until the symptoms subside. Persistent, uncontrolled diarrhea can cause such severe malnutrition, electrolyte imbalances and dehydration that it may ultimately result in death. Acute diarrhea is usually treated with fluid and electrolyte replacement, dietary modifications and antidiarrheal or antimicrobial agents. Acute diarrhea complications may cause severe illness, especially in high-risk groups, for example patients with underlying immunosuppression or advanced age. Antidiarrheal treatment is also required in patients with chronic diarrhea. Empiric therapies routinely used for chronic diarrhea include: stool-modifying agents (such as *psyllium* and fiber), anticholinergic agents, opiates, antibiotics, and probiotics.

Chronic diarrhea may be a symptom of a chronic disease, for example irritable bowel syndrome (IBS). It has been estimated that the prevalence of chronic diarrhea in the United States is approximately 5%. IBS alone is estimated to affect 15-20% of the U.S. population, and accounts for at least 30% of all gastroenterology health care costs. In many cases, the cause of the chronic diarrhea is not found, the diagnosis remains uncertain, and empiric treatments unsuccessful. Thus, there is an ongoing need for antidiarrheal agents that effectively stop or greatly reduce bowel movements and fluid loss in patients undergoing treatment, to remove the cause of diarrhea, or in patients in which the cause of diarrhea is not found.

H1 and H2 receptor antagonists are two classes of antihistamines. H1 receptor antagonists are used in the symptomatic treatment of multiple conditions, including allergic rhinoconjunctivitis, relief of pruritus in patients with urticaria, and in patients with chronic asthma. Newer H1 receptor antagonists, such as cetirizine, are referred to as second-generation H1 receptor antagonists, and are more selective for peripheral H1 receptors than first-generation H1 receptor antagonist, which antagonize both the central and peripheral nervous system H1 receptors as well as cholinergic receptors. The selectivity significantly reduces the occurrence of adverse drug reactions, such as sedation, while still providing effective relief of allergic conditions.

H2 receptor antagonists are used primarily to treat symptoms of acid reflux, or gastroesophageal reflux disease. H2 receptor antagonists reduce the production of stomach acid. Often diarrhea is listed as a major side effect of H2 receptor antagonists.

Diphenhydramine, a first-generation H1 receptor antagonist, together with either cimetidine or ranitidine, H2 receptor antagonists, have been studied for the treatment of acute allergic reactions. In a first study (Runge et al. "Histamine antagonists in the treatment of acute allergic reactions" *Ann Emerg Med* (March 1992) 21:237-242), patients were treated by a single intravenous administration of a solution 300 mg cimetidine and placebo, 50 mg diphenhydramine and placebo, or diphenhydramine plus cimetidine; the treatment was found effective for acute urticaria. In a second study (Lin et al. "Improved outcomes in patients with acute allergic syndromes who are treated with combined H1 and H2 antagonists" *Ann Emerg Med* (November 2000) 36:462-468), patients were treated by a single parenteral administration of a solution of either 50 mg diphenhydramine and saline or 50 mg diphenhydramine and 50 mg ranitidine; the treatment was found effective for acute allergic syndromes.

SUMMARY

In a first aspect, the present invention is a method of treating diarrhea in a patient, comprising administering an H1 receptor antagonist and an H2 receptor antagonist to the patient. Preferably, the H1 receptor antagonist comprises cetirizine and the H2 receptor antagonist comprises famotidine.

In a second aspect, the present invention is a method of treating diarrhea in a patient, comprising administering an H1 receptor antagonist and an H2 receptor antagonist to the patient. Preferably, the H2 receptor antagonist is not ranitidine.

In a third aspect, the present invention is a method of treating diarrhea in a patient, comprising administering an H1 receptor antagonist and an H2 receptor antagonist to the patient.

In a fourth aspect, the present invention is a method of treating diarrhea in a patient, comprising administering an H1 receptor antagonist and an H2 receptor antagonist to the patient. Preferably, the patient does not have mastocytic enterocolitis.

In a fifth aspect, the present invention is a pharmaceutical composition for treating diarrhea, comprising an H1 receptor antagonist, and an H2 receptor antagonist. Preferably, the H2 receptor antagonist is not ranitidine, and the pharmaceutical composition is an oral dosage form.

In a sixth aspect, the present invention is a pharmaceutical composition for treating diarrhea, comprising an H1 receptor antagonist, and an H2 receptor antagonist. Preferably, the H1 receptor antagonist is not diphenhydramine.

In a seventh aspect, the present invention is a pharmaceutical composition for treating diarrhea in a patient, comprising an H1 receptor antagonist, and an H2 receptor antagonist. Preferably, the patient does not have mastocytic enterocolitis.

In an eighth aspect, the present invention is use of an H1 receptor antagonist and an H2 receptor antagonist for the preparation of a medicament for treating a patient having diarrhea.

DEFINITIONS

The term "diarrhea," means increased fluidity or frequency of stools.

The term "acute diarrhea" is ongoing diarrhea which has occurred for at most 4 weeks.

The term "chronic diarrhea" is ongoing diarrhea for more than 4 weeks.

The term "unit dosage form," means a single pre-measured dose, and includes tablets, pills, capsules, packets, suspensions, transdermal patches, and rectal suppositories.

BRIEF DESCRIPTION OF THE DRAWINGS

FIG. 1 illustrates participants and responses by treatment group of an IBS-D study.

DETAILED DESCRIPTION

The present invention makes use of the discovery that administering an H1 receptor antagonist and an H2 receptor antagonist to a patient, results in a significant reduction or cessation of diarrhea. Applicant discovered that the combination of an H1 receptor antagonist and an H2 receptor antagonist administered to patients with diarrhea, resulted in 85-90% positive responders (see Example 7 and Table 1). A positive responder is identified as having a 50% or more reduction in the number of stools per day or a change in stool formation from liquid to solid. No adverse reactions or events were reported. A control group was treated with fiber (Metamucyl®) and an anticholinergic (Bentyl®); positive responders in the control group were less than 25%.

In a prior study (Jakate, et al., "Mastocytic Enterocolitis: Increased mucosal mast cells in chronic intractable diarrhea" *Arch Pathol Lab Med* (2006) 130:362-367), 33 patients who had increased mast cells (greater than 20 mast cells per high-power field) and were therefore identified by the authors as having "mastocytic enterocolitis," were administered a 2-week regimen of 10 mg per day of cetirizine hydrochloride (an H1 receptor antagonist) and 300 mg twice a day of ranitidine hydrochloride (an H2 receptor antagonist). In 8 of the 33 patients, a third drug, 200 mg/10 mL of cromolyn sodium (a mast cell mediator release inhibitor) was given 4 times daily for 4 to 6 weeks. The patients were followed for resolution, improvement, or persistence of symptoms. The patients who did not have mastocytic enterocolitis were not given these drugs. At follow-up, 22 (67%) of the 33 study patients showed cessation of diarrhea or significant reduction in diarrhea (defined as greater than or equal to 50% reduction in stool frequency or as greater than or equal to 50% improvement in stool consistency). However, because no control was used in the study, and because of the use of a third drug in some of the patients, it is not possible to determine how effective the treatment was for the selected patients. The placebo effect could account for up to about 11 of the patients with a positive outcome and the third drug could account for up to 8 of the patients with a positive outcome. The time frame of the follow-up was not provided. Furthermore, no statistical analysis or further studies were described.

The present invention includes treating diarrhea by administering an H1 receptor antagonist and an H2 receptor antagonist in combination. The present invention also includes unit dosage forms, multi-dosage forms, and kits, including an H1 receptor antagonist and an H2 receptor antagonist. Preferably, the H1 receptor antagonist includes cetirizine and the H2 receptor antagonist includes famotidine.

Diarrhea may be acute or chronic. Diarrhea may also be further classified:

Secretory diarrhea: diarrhea which occurs when the intestine does not complete absorption of water from luminal contents and electrolyte absorption is impaired, often caused by bacterial toxins, surgically reduced absorptive area of the intestines, microscopic colitis and luminal secretagogues such as laxatives and bile acids.

Osmotic diarrhea: diarrhea which results from intestinal malabsorption of ingested non-electrolytes.

Inflammatory diarrhea: diarrhea which may be characterized by blood and pus in the stool and possibly an elevated fecal calprotectin level, and inflammation exhibited on intestinal biopsy, caused by, for example, Crohn's disease and ulcerative colitis.

IBS-diarrhea predominate ("IBS-D"): chronic diarrhea associated with abdominal pain. In order to have IBS, a patient must have experienced onset of symptoms 6 months prior to diagnosis and must have recurrent abdominal pain or discomfort at least three days per month in the last three months associated with two or more of the following: improvement with defecation; onset associated with a change in frequency of stool; onset associated with a change in form of stool. Once IBS is diagnosed, it can be further classified based on the patients predominant symptom: diarrhea (IBS-D), or constipation (IBS-C), or mixed (IBS-M).

Functional diarrhea: chronic diarrhea in a patient who does not meet the criteria for IBS, and for which no other cause can be determined. This type of diarrhea may also be referred to as chronic idiopathic diarrhea.

Malabsorbtive diarrhea: diarrhea caused by an enteropathy such as celiac disease (celiac sprue) and giardiasis, which is characterized by excess gas, steatorrhea, and/or weight loss.

Drug induced diarrhea: diarrhea caused by a drug or treatment for an unrelated disease state, such as chemotherapy, radiation therapy, antibiotic therapy, anti-ulcer therapy, and herbal therapies.

Food intolerance diarrhea: diarrhea which is associated with dietary intake, such as lactose, sugar substitutes or other food substances.

Particularly common is IBS associated diarrhea, a chronic diarrhea, also referred to IBS-diarrhea predominate or simply "IBS-D". Some researchers claimed to have identified a subset of IBS-D, mastocytic enterocolitis, which they defined as a patient having greater than 20 mast cells per high-power field, based on an average of 10 high-power fields, for at least 2 separate biopsy pieces from random parts of the intestinal mucosa, using an original magnification of ×400, an objective having magnification of ×40 and an eyepiece having magnification of ×10 (Jakate, et al., "Mastocytic Enterocolitis: Increased mucosal mast cells in chronic intractable diarrhea" *Arch Pathol Lab Med* (2006) 130:362-367). In an aspect of the present invention, the patient does not have mastocytic enterocolitis.

H1 receptor antagonists block H1 histamine receptors; first-generation H1 receptor antagonists block histamine receptors in the central and peripheral nervous systems, as well as cholinergic receptors, while second-generation H1 receptor antagonists are selective for H1 histamine receptors in the peripheral nervous system. First-generation H1 receptor antagonists include brompheniramine, chlorpheniramine, dexbrompheniramine, dexchlorpheniramine, pheniramine, triprolidine, carbinoxamine, clemastine, diphenhydramine, pyrilamine, promethazine, hydroxyzine, azatadine, cyproheptadine, and phenindamine. Second-generation H1 receptor antagonists include ketotifen, rupatadine, mizolastine, acrivastine, ebastine, bilastine, bepotastine, terfenadine, quifenadine, azelastined, cetirizine, levocetirizine, desloratadine, fexofenadine and loratadine. Preferably, the H1 receptor antagonist is a second-generation H1 receptor antagonist, more preferably the H1 receptor antagonist is cetirizine or levocetirizine, with cetirizine being particularly preferred. Mixtures and combination of H1 receptor antagonists may also be used.

The H1 receptor antagonists may be used in an amount of from 0.1 to 10 times the amount typically used for the treatment of allergies, for example in an amount of 0.1 to 600 mg per dose, 0.5 to 500 mg per dose, 1.0 to 50 or 60 mg per dose, including 1.25, 1.5, 1.75, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 16, 17, 18, 19, 20, 25, 30, 35, 40 and 45 mg per dose. Preferably, the H1 receptor antagonist is administered 1, 2, 3 or 4 times per day. The H1 receptor antagonist may be administered as an injectable formulation, for example intravenously, intraparenterally or intramuscularly; transdermally, via a transdermal patch; or, preferably, orally, as a powder, table or capsule, an oral solution or suspension, or sublingual or buccal tablets. Alternative forms of administration include rectal suppositories, inhaled, epidural, subcutaneous, nasal spray, transmucosal, and intradermal formulations.

H2 receptor antagonists block H2 histamine receptors. H2 receptor antagonists include cimetidine, ranitidine, famotidine, and nizatidine, with famotidine being preferred. Mixtures and combinations of H2 receptor antagonists may also be used.

The H2 receptor antagonists may be used in an amount of from 0.1 to 10 time the amount typically used for treatment dyspepsia, for example 1.0 to 8000 mg per dose, 2.0 to 1000 mg per dose, 5.0 to 800 mg per dose, including 6.0, 7.0, 8.0, 9.0, 10, 15, 20, 21, 22, 22.5, 23, 24, 25, 26, 27, 28, 29, 30, 35, 40, 45, 50, 55, 60, 65, 70, 75, 80, 85, 90, 95, 100, 120, 140, 150, 175, 200, 250, 300, 350, 400, 450, 500, 600, and 700 mg per dose. Preferably, the H2 receptor antagonist is administered 1, 2, 3 or 4 times per day. The H2 receptor antagonist may be administered as an injectable formulation, for example intravenously, intraparenterally or intramuscularly; transdermally, via a transdermal patch; or, preferably, orally, as a powder, table or capsule, an oral solution or suspension, or sublingual or buccal tablets. Alternative forms of administration include rectal suppositories, inhaled, epidural, subcutaneous, nasal spray, transmucosal, and intradermal formulations.

Patients often respond to treatment within 48 to 72 hours. However, treatment should be carried out for an amount of time to resolve any underlying cause in the case of acute diarrhea, for example 3 to 14 days, or 5 to 10 days. In the case of chronic diarrhea, a 30 day trial is reasonable, and if the underlying cause of the diarrhea cannot be resolved, for example in the case of IBS-D, then treatment should be continued indefinitely.

Preferably, the H1 and H2 receptor antagonists are administered simultaneously, as a unit dosage form containing both receptor antagonists. Examples of unit dosage forms include oral compositions, such as tablets (for example, sublingual or buccal tablets), capsules (for example, hard gelatin and soft gelatin capsules), transmucosal and sublingual patches and films, pre-measured powder packets and saches, flavored and/or sweetened aqueous solutions or suspensions. Because diarrhea is often associated with dehydration, flavored and/or sweetened aqueous solutions or suspension may be oral rehydration solutions, or solutions which also contain sodium and glucose or a glucose-containing saccharide, in amounts of 250 ml, 500 ml or 1 liter of fluid. Furthermore, a pre-measured powder packet, containing the receptor antagonists, together with sodium (for example, as sodium chloride) and glucose or a glucose-containing saccharide, and optionally other excipients, flavorings and/or sweeteners, may be provided, which may be readily mixed with water prior to consumption. Preferably, the oral unit dosage form is present as a once-per-day dosage.

Examples of oral dosage forms include a tablet containing famotidine, in an amount of 5, 10, 15, 20, 22.5, 25, 30, 35 or 40 mg, as a core, and a coating of cetirizine, in an amount of 2.5, 5, 8.5, 10, 15, or 20 mg. Another example includes a capsule containing granules of famotidine and cetirizine in water-soluble matrix. In another example, both the famotidine and the cetirizine are present as a mixture in a matrix, either as a table or within a capsule. In these examples, other H1 and/or H2 receptor antagonists may be used in place of, or in addition to, famotidine and/or cetirizine.

Other unit dosage forms may also be provided, containing both H1 and H2 receptor antagonist. For example, injectable formulation containing a sterile solution or suspension, including formulation for administration intravenously, intraparenterally or intramuscularly, may be provided. A unit dosage form for administration transdermally, via a transdermal patch, may be provided. Other unit dosage forms include rectal suppositories, inhaled, epidural, subcutaneous, nasal spray, and intradermal formulations. Excipients and adjuvants maybe also be included in any of the unit dosage forms, both oral and non-oral.

Multi-dosage forms, such as kits, containing 2 to 30, 3 to 25, or 5 to 14 unit dosage forms, for example 6, 7, 8, 9, 10, 11, 12, 13, 15, 20, 40, 50 or 60 unit dosage forms, may be provided. Preferably, the multi-dosage forms contain sufficient unit dosage forms for administration over a period of 2 to 30, 3 to 25, or 7 to 14 days, for example 4, 5, 6, 7, 8, 9, 10, 11, 12, 13, 20 or 30 days. Kits may also be provided, which include oral rehydration solutions, or powders which may be hydrated to form oral rehydration solutions, or kits containing sodium and glucose or a glucose-containing saccharide, as well as other excipients, flavorings and/or sweeteners, together with unit dosage forms.

EXAMPLES

Example 1

Treatment of Secretory Diarrhea

Patient #1, age 65, was hospitalized for more than one week for weight and fluid loss related to chronic diarrhea. The patient had from 20 to 40 stools per day and severe life threatening diarrhea. The patient was treated with 20 mg famotidine and 10 mg cetirizine, once per day. Symptoms subsided within 48 hours with a 95% decrease in the number of stools and the patient was discharged. The patient responded to treatment and now has 1 stool per day, occasionally two, but no diarrhea.

Example 2

Treatment of IBS Diarrhea

Seven patients, age 26 to 80, were treated for mild to severe diarrhea, ranging from 3 to 18 stools per day.

Patient #1, age 80, with mild to severe cramping and 4 to 5 stools a day. The patient was treated with 300 mg ranitidine and 10 mg cetirizine, once per day. The patient reported a 60% reduction in the number of stools.

Patient #2, age 62, had severe weight loss, greater than 30 pounds, related to the diarrhea, 10 to 20 stools per day, and was opiate and steroid dependant. The patient was treated with 20 mg famotidine and 10 mg cetirizine, once per day.

Treatment was successful with an 85 to 90% reduction in the number of stools. The patient now has 1 to 2 stools per day for over 8 months on treatment.

Patient #3, age 65, prior to treatment was homebound, had 4 to 5 stools per day, each episode lasting an hour or two. The patient was treated with 300 mg ranitidine and 10 mg cetirizine, once per day. Treatment was successful, with the patient reporting a 90% reduction in the number of stools.

Patient #4, age 67, with moderate diarrhea and cramping, had 4 to 5 stools per day. The patient was treated with 20 mg famotidine and 10 mg cetirizine, once per day. Treatment was successful, with a 75% reduction in the number of stools, no cramping and no side effects.

Patient #5, age 26, had moderate to severe diarrhea with 7 to 8 stools per day. The patient was treated with 20 mg famotidine and 10 mg cetirizine, once per day. Treatment was successful, with a decrease in the number of stools by 50%, down to 3 to 4 per day, with no side effects.

Patient #6, age 74, with severe diarrhea, had 8 stools per day and was homebound. The patient was treated with 300 mg ranitidine and 10 mg cetirizine, once per day. Treatment was successful, with a decrease in the number of stools by 75%, down to 2 stools per day and no side effects. Patient is presently only on cetirizine.

Patient #7, age 51, with colon resection, had severe diarrhea with 15 to 20 stools per day. The patient was treated with 300 mg ranitidine and 10 mg cetirizine, once per day. Treatment was successful, with a decrease in the number of stools by 94%, to 1 to 2 stools per day and better consistency, with no side effects.

Example 3

Chronic Idiopathic Diarrhea

A patient, age 81, with a complaint of moderate diarrhea and no additional diagnoses, had 4 to 6 stools per day, causing interference with activity level and lifestyle. The patient was treated with 20 mg famotidine and 10 mg cetirizine, once per day. Treatment was successful, with a decrease in the number of stools by 70%, to 1 to 2, mostly 1, per day and a repeat colonoscopy was cancelled because symptoms had resolved.

Example 4

Chemotherapy Induced Diarrhea

Patient, age 64, with colon cancer and moderate to severe diarrhea, in a deconditioned state from chemotherapeutic agents, had 5 to 10 stools per day. The patient was treated with 20 mg famotidine and 10 mg cetirizine, once per day. Treatment was successful, with a decrease in the number of stools by 80%, to 1 to 2 per day and normal consistency, with no side effects.

Example 5

Inflammatory Diarrhea—Ulcerative Colitis/Crohn's Disease

Three patients, age 35-64, were treated for severe diarrhea related to ulcerative colitis or Crohn's disease.

Patient #1, age 64, with Crohn's disease, had 12 to 15 stools per day and severe diarrhea. The patient was treated with 20 mg famotidine and 10 mg cetirizine, once per day. Treatment was not successful, with a decrease in the number of stools only by 5%. There were no side effects.

Patient #2, age 37, with Crohn's disease and colitis, had severe diarrhea with 4 to 5 stools per day. The patient was treated with 300 mg ranitidine and 10 mg cetirizine, once per day. Treatment was successful, with a decrease in the number of stools by 75%, to one stool per day and normal consistency. There were no side effects.

Patient #3, age 35, with ulcerative colitis, had severe diarrhea with 4 to 6 stools per day. The patient was treated with 20 mg famotidine and 10 mg cetirizine, once per day. Treatment was successful, with a decrease in the number of stools by 50%. There were no side effects.

Example 6

Celiac Disease

Patient #1, age 57, with celiac disease had mild to moderate diarrhea, with 2 to 4 stools per day. The patient had no improvement from treatment with 20 mg famotidine and 10 mg cetirizine, once per day. There were no side effects.

Patient #2, age 26, with celiac disease. The patient had little improvement from treatment.

Example 7

IBS-D Treatment Study

The study population age was 18 to 80, with the patients having chronic unexplained diarrhea from an outpatient population of a clinic and outpatients from a medical center, who gave consent for treatment. Patients were excluded who had a history of systemic or cutaneous mastocytosis, definable etiology of diarrhea (other than IBS-D or chronic idiopathic diarrhea) such as celiac disease, inflammatory bowel disease, or lactose intolerance, or who were pregnant. The study was initiated after IRB approval.

Upon referral to the study coordinator, and after informed consent was obtained, patients were assigned to one of the two study arms. Patients underwent colonoscopy with biopsies that were then evaluated by a pathologist who was blind to the study arm. The study coordinator reviewed pathology results and documents accordingly. The patient was provided the treatment method that was randomly assigned and given a diary to document symptoms. Follow up phone conversations and a return visit was scheduled. At the completion of the four week medication treatment period, a telephone call or visit was carried out. At eight weeks, the diary was returned and the coordinator documented the data recorded by the subjects. There was a process for adverse event reporting and to date, no adverse reactions or events have been reported.

One study arm received famotidine (20 mg per day) and cetirizine (10 mg per day), once per day. The second study arm received fiber (Metamucil®) and an anticholinergic (Bentyl®) once per day. Table 1 shows the results of the study. Tables 2 and 3 show the statistical analysis of the study results.

TABLE 1

Study results

| Treatment Group | Number of Participants | Positive Responders | Non-Responders | Percent Responding |
| --- | --- | --- | --- | --- |
| famotidine and cetirizine | 26 | 25 | 1 | 96% |

TABLE 1-continued

Study results

| Treatment Group | Number of Participants | Positive Responders | Non-Responders | Percent Responding |
|---|---|---|---|---|
| dicylcomine and psyllium | 8 | 2 | 6 | 25% |

Positive responders = Appreciable decrease in # of stools per day
Non-responders = No appreciable decrease in # of stools per day

TABLE 2

Group statistics

| Treatment Group | N | Mean | Std. Deviation | Std. Error Mean |
|---|---|---|---|---|
| dicylcomine and psyllium | 8 | 0.13 | 0.354 | 0.125 |
| famotidine and cetirizine | 26 | 1.00 | 0.000 | 0.000 |

TABLE 3

Independent samples test
Independent Samples Test

| | Levene's Test for Equality of Variances | | t-test for Equality of Means | | | | | | |
|---|---|---|---|---|---|---|---|---|---|
| | | | | | | | | 95% Confidence Interval of the Difference | |
| Status | F | Sig. | t | df | Sig. (2-tailed) | Mean Difference | Std. Error Difference | Lower | Upper |
| Equal variances assumed | 19.033 | 0.000 | −13.088 | 32 | 0.000 | −8.75 | 0.67 | −1.011 | −.739 |
| Equal variances not assumed | 19.033 | 0.000 | −7.000 | 7.000 | 0.000 | −8.75 | 0.125 | −1.171 | −.579 |

FIG. 1 illustrates participants and responses by treatment group. The bars on the left represent the patients who received famotidine and cetirizine, while the bars on the right represent the patients who received fiber and anticholinergic. As indicated in the table and the figure, 90% of the patients receiving famotidine and cetirizine responded to the treatment, while only 10% of those receiving fiber and anticholinergic responded to the treatment.

Tables 4 and 5 show the percent decrease in number of stools per day, for the famotidine and cetirizine study arm, and the dicylcomine and psyllium study arm, respectively.

TABLE 4

Percent decrease in number of stools per day, for the famotidine and cetirizine study arm

| Number of Subjects | Percent Stool Decrease |
|---|---|
| 1 | 0% |
| 1 | 10-25% |
| 2 | 28-45% |
| 11 | 50-65% |
| 11 | 66-85% |
| 0 | >86% |

TABLE 5

Percent decrease in number of stools per day, for the dicylcomine and psyllium study arm

| Number of Subjects | Percent Stool Decrease |
|---|---|
| 6 | 0% |
| 0 | 10-25% |
| 1 | 28-45% |
| 1 | 50-65% |
| 0 | 66-85% |
| 0 | >86% |

Example 8

Chronic Diarrhea Treatment Study

The study population age was 21 to 70, with patients diagnosed with chronic diarrhea, who gave consent for treatment. Patients were excluded if there was a sensitivity or allergy to H1 receptor antagonists or H2 receptor antagonists, renal impairment or a history of renal failure, a diagnosis of inflammatory bowel disease (Crohn's disease or ulcerative colitis), a known active infection of the colon (such as *Clostridium difficile*, giardia, or *Salmonella*), biopsy proven microscopic colitis (collagenous or lymphocytic colitis), or an inability to discontinue other anti-diarrheal agents during the study. Patients were also excluded if they were pregnant or lactating women, or if the patient was taking atazanavir, itraconazole, or ketoconazole. The study was initiated after IRB approval.

The study was a 4-week randomized, double-blind, controlled trial, with crossover. After informed consent was obtained, patients were randomly assigned to one of the two groups (active or placebo), with neither the patients nor the physicians knowing to which group each patient was assigned. Each patient was provided the treatment method that was randomly assigned and given a diary to document symptoms. After 7 days of treatment, subjects participated in a telephone interview with a blinded member of the research team. Crossover was allowed after one week of treatment for non-responders. At the end of the 28 day study, the patients completed a detailed questionnaire. Stool quality was evaluated using the 7 point Bristol Stool Scale.

The "active" group received famotidine (24 mg) and cetirizine (9 mg), once per day, with both drugs combined in the form of a single capsule. The "placebo" group received a capsule once per day, which contained no active ingredients.

The results of the study are shown in Table 6. The table shows the results of 27 patients, 12 in the placebo group and 15 in the active group. The average value for percent change is stools per day (SPD) was 25.08 for the placebo group, while the average value for percent change in SPD was 46.00 for the active group. Only 3 of the active group patients agreed to crossover, while 9 of the placebo group patients agreed to crossover. The data demonstrate a clinical significance between the placebo group and the active group, and demonstrate a significant improvement in the quality of life of the patients in the active group.

TABLE 6

Results of Chronic Diarrhea Treatment Study

| Group | Number of Patients | Mean Δ% SPD |
|---|---|---|
| Placebo | 12 | 25.08 |
| Active | 15 | 46.00 |

REFERENCES

Schiller L R, "Secretory Diarrhea" *Current Gastroenterology Reports* (1999) 1:389-397.

Schiller, L R, Hogan R B, Morawski, S G, Santa Ana, Calif., Bern M J, Nogaard, R P, Bo-Linn, G W, Fordtran J S, "Studies of the Prevalence and Significance of Radiolabeled Rice Acid Malabsorption in a Group of Patients with Idiopathic Chronic Diarrhea" *Gastroenterology* (1997) 92:151-160.

Fordtran J S, Santa Ana Calif., Morawski S G, et al. "Pathophysiology of chronic diarrhea: insights derived from intestinal perfusion studies in 31 patients" *Gastroenterol Clin North Am* (1986) 15:477-490.

Lunardi C, Bambara L M, Biasi D, et al. "Double-blind cross-over trial of oral sodium cromoglycate in patients with irritable bowel syndrome due to food intolerance" *Clin Exp Allergy* (1991) 21: 569-572.

Fine K D, Schiller U R, "AGA technical review on the evaluation and management of chronic diarrhea" *Gastroenterology* (1999) 116:1464-1486.

O'Sullivan et al. "Increased mast cells in the irritable bowel syndrome" *Neurogastroenterol. Mot.* (2000) 12:449-457.

Spiller R C, Jenkins D, Thornley J P, Hebden J M, Wright T, Skinner M, Neal K R, "Increased rectal mucosal enteroendocrine cells, T lymphocytes, and increased gut permeability following acute *Campylobacter* enteritis and in post-dysenteric irritable bowel syndrome" *Gut* (December 2000) 47(6): 804-11.

Theoharides T C Cochrane D E, "Critical role of Mast Cells in inflammatory diseases and the effect of acute stress" *J Neuroimmunol* (2004) 146:1-12.

Barbars G, De Giorgio et al. "New pathophysiological mechanisms in irritable bowel syndrome" *Aliment Pharmacol Ther* (2004) 20(suppl. 2):1-9.

Dunlop S P, Hebden et al. "Abnormal intestinal permeability in subgroups of diarrhea-predominant irritable bowel syndromes" *Am J Gastroenterol* (2006) 101(6):1288-1294.

Barbara G, Stanghellini V et al. "Functional gastrointestinsl disorders and mast cells: implications for therapy" *Neurogastroenterol Motil* (2006) 18:6-17.

Halvorson H A et al. "Postinfectious irritable bowel syndrome-a meta-analysis" *Am J Gastroenterol* (2006) 101: 1894-1899.

Posserud I et al. "Small intestinal bacterial overgrowth in patients with irritable bowel syndrome" *Gut* (2007) 56:802-808.

Lewis, J, Candelora, J, Hogan, I I, RB, Briggs, F, Abraham, S, "Crystal-Storing Histiocytosis Due to Massive Accumulation of Charcot-Leyden Crystals: A Unique Association Producing Colonic Polyposis in a 78-year-old Woman With Eosinophilic Colitis" *Am J Surg Pathol.* (March 2007) 321(3):481-485.

Jakate S, et al. "Mastocytic enterocolitis increased mucosal mast cells in chronic intractable diarrhea" *Arch Pathol Lab Med*, (2006) 130:362-367.

Kirsch R H, Riddell R, "Histopathological alterations in irritable bowel syndrome" *Modem Pathology* (2006) 19:1638-1645.

Ramos L, Vicario M, Santos J, "Stress-mast cell axis and regulation of gut mucosal inflammation: from intestinal health to an irritable bowel" *Med Clin (Barc)* (June 2007) 129(2):61-69.

Piche T, Saint-Paul M C et al. "Mast cells and cellularity of the colonic mucosa correlated with fatigue and depression in irritable bowel syndrome" *Gut* (2008) 57:468-473.

Visser J, Rozing et al. "Tight Junctions, intestinal permeability and autoimmunity celiac disease and type 1 diabetes paradigms" *Ann NY Acad Sci* (2009) 1165:195-205.

Walker M M, Talley N J, et al. "Duodenal mastocytosis, eosinophilia and intraepithelial lymphocytosis as possible disease merkers in the irritable bowel syndrome and functional dyspepsia" *Aliment Pharmacol Ther* (2009) 29:765-773.

Thabane M, Marshall J K, "Post-infectious irritable bowel syndrome" *World J Gastroenterol.* (2009) 15(29):3591-3596.

Walker M M, Salehian S S et al. "Implications of eosinophilia in the normal duodenal biopsy—an association with allergy and functional dyspepsia" *Aliment Pharmacol Ther* (2010) 31:1229-1236.

Klooker T K, Braak B, Koopman K E et al. "The mast cell stabilizer ketotifen decreases visceral hypersensitivity and improves intestinal symptoms in patients with irritable bowel syndrome" *Gut* (2010) 59:1213-21.

Martinez C, et al. "The Jejunum of Diarrhea-Predominant Irritable Bowel Syndrome Shows Molecular Alterations in the Tight Junction Signaling Pathway That Are Associated With Mucosal Pathobiology and Clinical Manifestations" *Am J Gastroenterol* (2012) 107:736-746.

Theoharides T C, Shahrzad A, Chen J, Huizinga J, "Irritable Bowel Syndrome and the Elusive Mast Cell" *Am J Gastroenterol* (2012) 107:727-729.

Smith M J, "IBS remains a mysterious disorder with few effective Remedies" *Gastroenterology and Endoscopy News* (April 2012) Vol. 63:4.

Pyleris E, Giamarellos-Bourboulis E J, et al. "The prevalence of overgrowth by aerobic bacteria in the small intestine by small bowel culture: relationship with irritable bowel syndrome" *Dig Dis Sci.* (May 2012) 57(5):1321-9.

Vivinus-Nebot M, Dainese R, et al. "Combination of allergic factors can worsen diarrheic irritable bowel syndrome: role of barrier defects and mast cells" *ACG* (2012) 107:74-81

Akhavein A, Patel N R, et al. "Allergic Mastocytic Gastroenteritis and colitis: and unexplained etiology in chronic abdominal pain and gastrointestinal dysmotility" *Gastroenter Research and Practice* (2012) 2012:950582.

Martinez C, Lobo B, et al. "Diarrhoea-predominant irritable bowel syndrome: an organic disorder with structural abnormalities in the jejunal epithelial barrier" *Gut* (2012) [Epub ahead of print: 25 May 2012].

Braak B, Klooker T K et al. "Mucosal immune cell numbers and visceral sensitivity in patients with irritable bowel syndrome: is there any relationship?" *Am J Gastroenterol* (2012) 107:715-726.

Theoharides T C, Asadi S, Chen J, Huizinga J D, "Irritable bowel syndrome and the elusive mast cells" *Am J Gastroenterol* (2012) 107(5):727-729.

Farhadi A, Fields J Z, Keshavarzian A, "Mucosal mast cells are pivotal elements in inflammatory bowel disease that connect the dots: stress, intestinal hyperpermeability and inflammation" *World J Gastroenterol* (2007) 13(22):3027-3030.

Juckett G, Trivedi R, "Evaluation of chronic diarrhea" *American Family Physician* [serial online]. Nov. 15, 2011; 84(10):1119-1126.

*Diarrhea* [*electronic resource*] *National Digestive Diseases Information Clearinghouse.* (2011). Bethesda, Md.: U.S. Dept. of Health and Human Services, National Institutes of Diabetes and Digestive and Kidney Diseases.

Forbes D, O'Loughlin E, Scott R, Gall D, "Laxative abuse and secretory diarrhoea" *Arch Dis Child* (1985) 60(1):58-60.

DuPont, H. L. et al., "Diarrhea", *National Digestive Diseases Information Clearinghouse*, January 2012.

Lever, D. D., et al., "Acute Diarrhea", *Center for Continuing Education publications: Disease Management Project*, Cleveland Clinic, Aug. 1, 2010.

H2 blockers, *MedlinePlus®*, U.S. National Library of Medicine, NIH, updated: Aug. 11, 2011.

Runge et al. "Histamine antagonists in the treatment of acute allergic reactions" *Ann Emerg Med* (March 1992) 21:237-242.

Lin et al. "Improved outcomes in patients with acute allergic syndromes who are treated with combined H1 and H2 antagonists" *Ann Emerg Med* (November 2000) 36:462-468.

He, Shuang; Li, Feng; Zhou, Dan; Du, Junrong; Huang, Yuan, Drug development and industrial pharmacy, (October 2012) 38(10)1280-1289.

Akin C, Valent P, Metcalfe D D "Mast cell activation syndrome: Proposed diagnostic criteria" *J Allergy Clin Immunol.* (2010) 126(6):1099-104.

Hamilton M J, Hornick J L, Akin C, Castells M C, Greenberger N J "Mast cell activation syndrome: a newly recognized disorder with systemic clinical manifestations" *J Allergy Clin Immunol.* (2011) 128(1):147-152.

Valent P "Mast cell activation syndromes: definition and classification" *Allergy* (2013) [Epub ahead of print 15 Feb. 2013].

What is claimed is:

1. A method of treating diarrhea in a patient, comprising administering an H1 receptor antagonist and an H2 receptor antagonist to the patient, wherein the patient does not have mastocytic enterocolitis, the patient has IBS-D, the H1 receptor antagonist is cetirizine, levocetirizine, or mixtures thereof, and the H2 receptor antagonist is famotidine.

2. The method of claim 1, wherein the H1 receptor antagonist and the H2 receptor antagonist are administered simultaneously.

3. The method of claim 1, wherein the H1 receptor antagonist and the H2 receptor antagonist are administered once per day for at least 2 days.

4. The method of claim 1, wherein the patient has chronic diarrhea.

5. The method of claim 1, wherein the famotidine is administered in an amount of 10 to 40 mg.

6. The method of claim 1, wherein the cetirizine, levocetirizine or mixtures thereof is administered in an amount of 5 to 20 mg.

7. The method of claim 1, wherein the H1 receptor antagonist and the H2 receptor antagonist are administered once per day for at least 7 days.

8. The method of claim 2, wherein the cetirizine, levocetirizine, or mixtures thereof is administered in an amount of 5 to 20 mg, and the famotidine is administered in an amount of 10 to 40 mg.

9. The method of claim 8, wherein the cetirizine, levocetirizine, or mixtures thereof and the famotidine are administered together as a unit dosage form.

10. The method of claim 1, wherein the cetirizine, levocetirizine, or mixtures thereof and the famotidine are administered together as a unit dosage form.

11. A method of treating IBS-D in a patient, comprising: administering an H1 receptor antagonist and an H2 receptor antagonist to the patient, wherein, the H1 receptor antagonist is cetirizine, levocetirizine, or mixtures thereof, the H2 receptor antagonist is famotidine, and the patient does not have mastocytic enterocolitis.

12. The method of claim 11, wherein the patient has chronic diarrhea.

13. The method of claim 11, wherein the H1 receptor antagonist and the H2 receptor antagonist are administered simultaneously.

14. The method of claim 11, wherein the cetirizine, levocetirizine, or mixtures thereof and the famotidine are administered together as a unit dosage form.

15. The method of claim 13, wherein the cetirizine, levocetirizine, or mixtures thereof is administered in an amount of 5 to 20 mg, and the famotidine is administered in an amount of 10 to 40 mg.

16. The method of claim 11, wherein the famotidine is administered in an amount of 10 to 40 mg.

17. The method of claim 11, wherein the cetirizine, levocetirizine or mixtures thereof is administered in an amount of 5 to 20 mg.

* * * * *